United States Patent [19]

Imondi et al.

[11] 4,143,130

[45] Mar. 6, 1979

[54] METHOD FOR TREATING KIDNEY STONES

[75] Inventors: Anthony R. Imondi, Doylestown; Richard L. Wolgemuth, Hatfield, both of Pa.

[73] Assignee: Warren-Teed Laboratories, Inc., Columbus, Ohio

[21] Appl. No.: 828,397

[22] Filed: Aug. 29, 1977

[51] Int. Cl.$^2$ ............... A61K 31/78; A61K 31/74
[52] U.S. Cl. ........................... 424/81; 424/79
[58] Field of Search ................... 424/79, 81

[56] References Cited

U.S. PATENT DOCUMENTS

| 2,798,053 | 7/1957 | Brown | 424/81 |
| 3,184,381 | 5/1965 | Ashmead | 424/79 |
| 3,224,941 | 12/1965 | Nash et al. | 424/78 |
| 3,330,729 | 7/1967 | Johnson | 424/81 |
| 3,842,022 | 10/1974 | Wang | 424/81 |
| 3,957,973 | 5/1976 | Yamaguchi et al. | 424/81 |

*Primary Examiner*—Donald B. Moyer
*Attorney, Agent, or Firm*—Marion C. Staves

[57] ABSTRACT

Water soluble and colloidially water soluble polymers of carboxylic acid-containing monomers useful for treating kidney stones are disclosed.

8 Claims, No Drawings

METHOD FOR TREATING KIDNEY STONES

This invention relates to pharmaceutical compositions containing soluble and colloidally water soluble carboxylic acid polymers and to methods of using them to treat kidney stones. Biological studies employing rats as the test animal show that the compositions of this invention are useful in binding calcium and dissolving kidney stones.

In the United States alone, there are each year about 250,000 newly diagnosed patients with all types of kidney stones. Analysis of these stones shows that 70% of all kidney calculi contain calcium. Although there is no unanimously accepted regimen for urolthiasis, reduction in urinary calcium excretion is one means of ston prophylaxis.

Highly substituted sodium cellulose phosphate is presently being studied clinically and appears to be useful in the treatment for calcium calculi (Pak, et al., *New England J. Med.* 290:4 (1974)). This material also binds intestinal calcium. The increase in fecal calcium with sequestrant therapy is accompanied by lower urinary calcium output. In essence, by increasing the fecal calcium load, calcium sequestrants decrease the calcium load on the kidney.

Although cellulose phosphate is clinically effective, the suggested regimen is 15-19 grams. By contrast, the soluble and swellable carboxylic acid polymers of this invention have a 3-4 fold increase in in vitro capacity and will be effective at much lower doses.

This invention is based upon the well established fact that patients with urolithiasis can be treated successfully with calcium restricted diets. Ordinarily, large amounts of calcium in the intestine are absorbed and excreted via the kidney. The polymers of this invention interrupt this process by binding large amounts of the calcium thereby preventing calcium absorption and reducing the urinary calcium load.

The binding and removal of calcium by highly cross-linked, nonswellable carboxylic resins is known and has been used in the removal of calcium from water and blood. In 1968, Burghele, et al., (Urologe, 6:234 (1968)) introduced the use of resins as a means of renal stone prophylaxis; however, no active resin has been discovered which will reduce kidney stone formation. In fact, Lurie, et al. (*Investigative Urology*, Vol. 13, No. 4, (1976)) found that resin Dowex 50WX8 was ineffective in binding calcium in the gastrointestinal tract.

The soluble noncrosslinked polymers and the lightly crosslinked colloidally water soluble polymers (swelling index greater than 10) having carboxylic acid groups of this invention are effective as calcium sequestrants. In addition, soluble polymers offer many advantages from a dosage standpoint since they can be administered as liquids.

The water soluble and colloidally water soluble carboxylic acid polymers also promote phosphate absorption, a desirable goal in patients with kidney stones since high levels of urinary phosphate enhance the solubility of the urinary calcium.

The compositions useful in this invention are water soluble and colloidally water soluble polymers prepared from olefinically unsaturated carboxylic acid containing at least one activated carbon-to-carbon double bond and at least one carboxy group, that is, an acid containing an olefinic double bond which readily polymerizes because it is in the alpha-beta position with respect to a carboxy

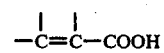

or as a part of a terminal methylene grouping thusly: $CH_2=C<$.

In the alpha-beta acids the close proximity of the strongly polar carboxy group to the double-bonded carbon atoms has a strong activating influence rendering the substances containing this structure very readily polymerizable. Likewise, the presence of the terminal methylene grouping in a carboxylic monomer makes this type of compound much more easily polymerizable than if the double bond were intermediate in the carbon structure. Olefinically-unsaturated acids of this broad class includes such widely divergent materials as the acrylic acids including acrylic acid, methacrylic acid, ethacrylic acid, α-chloroacrylic acid, α-cyanoacrylic acid, and the like, crotonic acid, β-acryloxypropionic acid, hydrosorbic acid, sorbic acid, α-chlorosorbic acid, cinnamic acid, β-styrylacrylic acid (1-carboxy-4-phenylbutadiene-1,3)-hydromuconic acid, itaconic acid, citraconic acid, mesaconic acid, muconic acid, glutaconic acid, aconitic acid and the like.

As used herein, the term "carboxylic acid" includes polycarboxylic acids and those acid anhydrides such as maleic anhydride, wherein the anhydride group is formed by the elimination of one molecule of water from two carboxy groups located on the same polycarboxylic acid molecule. Anhydrides of the types formed by elimination of water from two or more molecules of the same or different unsaturated acids, such as acrylic anhydride, are not included because of the strong tendency of their polymers to hydrolyze in water and alkali.

It is ordinarily desirable to utilize, as the carboxylic monomer, one or more α,β-unsaturated carboxylic acids containing at least one carboxy group, with the olefinic double bond alpha-beta to at least one carboxy group. Illustrative alpha-beta unsaturated carboxylic acids of this nature include the acrylic acids disclosed above and in addition beta-methylacrylic acid, (crotonic acid), alpha-phenylacrylic acid, and others, hydrosorbic acid, alpha-butylcrotonic acid, angelic acid, cinnamic acid, m-chlorocinnamic acid, p-chlorocinnamic acid, umbellic acid, and other monoolefinic monocarboxylic acids; maleic acid, fumaric acid, hydromuconic acid, glutaconic acid, itaconic acid, citraconic acid, mesaconic acid, tricarboxy ethylene, tetracarboxy ethylene and other monolefinic di- and polycarboxylic acids; sorbic acid, beta-acryloxyacrylic acid, beta-styrylacrylic acid (4-phenyl-1-carboxybutadiene-1,3) and other polyolefinic monocarboxylic acids; 3-carboxypentadiene-(2,4)-oic-1, muconic acid, and other polyolefinic polycarboxylic acids; and maleic anhydride and other acid anhydrides having the general structure:

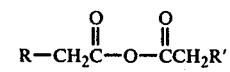

wherein R and R' are selected from hydrogen, alkyl, for example, lower alkyl containing from 1 to 10 carbon atoms such as methyl, ethyl, propyl, butyl, pentyl, hexyl, heptyl, octyl, nonyl, decyl and the like, halo, cyano, hydroxy, lactam and lactone groups, aryl, such as phenyl, tolyl, xylyl and the like, aralkyl such as benzyl and the like, or cycloalkyl, for example, cyclobutyl, cyclopentyl, cyclhexyl and the like.

The preferred carboxylic monomers for use in this invention are the monoolefinic acrylic acids having the general structure:

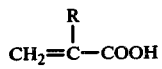

wherein R is a substituent selected from hydrogen, halo, hydroxy, lactone, lactam, cyano, alkyl, monovalent aryl, monovalent aralkyl, monovalent alkaryl and monovalent cycloaliphatic. Illustrative acrylic acids of this preferred class are acrylic acid itself, methacrylic acid, ethacrylic acid, chloroacrylic acid, bromoacrylic acid, cyanoacrylic acid, alpha-phenylacrylic acid, alpha-benzylacrylic acid, alpha-cyclohexylacrylic acid and the like. Alpha-haloacrylic acids readily hydrolyze at the halogen substitution with the formation of hydroxy and lactone groups. Of this class, acrylic acid itself is most preferred because of its generally lower cost, ready availability and ability to form superior polymers. Another particularly preferred carboxylic monomer is maleic anhydride.

When crosslinkers are employed (i.e., the amount of crosslinker which forms part of the molecule and is therefore another monomer), they are generally employed in the range of from about 0.01% to about 5% and preferably employed in the range of from about 0.1% to about 2.0% by weight of the monomer(s) employed. Crosslinkers which can be employed include 1,1,1-trimethylolpropane trimethacrylate, styrene, vinylcrotonate, vinylacetate, polyallylsucrose, polyallylpentaerythritol and the like.

The degree of polymerization can be in the range of from about 10 to about 100,000 and is usually in the range of from about 40 to about 3,000.

The colloidally water soluble products of this invention have a swelling index (S.I.) much greater than ion exchange resins (S.I. for ion exchange resins = 2 or 3) and can be in the range of from about 10 to about 1500 but usually are in the range of from about 100 to about 500. The term "colloidally water soluble" means that the crosslinked products are not true solutions but are colloidal suspensions. Although none of the material will settle upon standing, but ultra-centrifuging most of the material may be separated.

The compounds are administered at a unit dosage in the range of from about 0.1 g. to about 20 g.

The compositions containing the carboxylic acid-containing polymers or its salts as the active ingredients and also the polymers or its salts themselves are agents which can be administered in a wide variety of the therapeutic dosages in conventional vehicles. The products may be administered in a wide variety of pharmaceutically acceptable carriers, for example, in a flavored aqueous solution subdivided into three or four doses per day. Typical formulations contain from about 10% to about 20% of the product in a suitably flavored, colored, thickened, preserved, aqueous mixture. The liquid dosage form may contain, in addition to water, small amounts of ethanol or other pharmaceutically acceptable solvent or solvents. Other dosage forms include gels prepared with pectin, agar, hydroxyethylcellulose or other approved gelling agents, tablets, capsules, pills, which may be microencapsulated, or enterically coated.

In addition, formulations may contain combinations of drugs particularly suited to the treatment of kidney stones and relief of pain. Other oral drug combinations are also within the scope of this invention.

The oral daily dosage of the products may be varied over a wide range varying from about 10 mg. to about 400 mg./kg./day. The product can be administered in subdivided doses in the form of scored tablets or capsules; however, for the soluble polymers, liquid dosage forms are preferred. These dosage forms permit the symptomatic adjustment of the dosage to the patient to be treated. An effective amount of the drug is ordinarily supplied at a unit dosage level of from about 10 mg. to about 400 mg./kg. of body weight. Preferably, the range is from about 20 mg. to 150 mg./kg. of body weight/day.

The following examples are illustrative of how to prepare various compositions containing the active ingredients of this invention. However, said examples are merely illustrative and should not be construed as limiting the scope of this invention.

EXAMPLE A — Tablets Containing 500 mg. of Active Ingredient Per Tablet

|  | Per Tablet |
|---|---|
| Polyacrylic acid MW = 400,000 | 500 mg. |
| Sodium Phosphate Dibasic | 73 mg. |
| Lactose | 70 mg. |
| Corn Starch | 50 mg. |
| Magnesium Stearate | 7 mg. |

Weigh and pass each ingredient through a No. 40 mesh screen (U. S. Sieve). Blend the ingredients in a twin-shell blender for 10 minutes. Compress tablets to a weight of 700 mg. per tablet on a tablet machine.

EXAMPLE B — Oral Elixir Dosage Form Containing 500 mg. of Active Ingredient Per Five ml.

|  | Per 5 ml. |  |
|---|---|---|
| Polyacrylic acid MW = 400,000 | 750 | mg. |
| Sorbitol Solution 70% W/W | 1000 | mg. |
| Ethyl Alcohol | 500 | mg. |
| Propylparaben | 5 | mg. |
| FD & C Yellow No. 5 | 0.2 | mg. |
| Flavoring Agent | 0.03 | mg. |
| Purified Water | qs |  |

Polyacrylic acid is dissolved in a portion of water by gentle agitation. The sorbitol is added to this solution. The FD & C No. 5 is dissolved in a portion of water and added to the above solution. The propylparaben is dissolved in a portion of ethyl alcohol. The flavoring agent is dissolved in the remaining ethyl alcohol. The two ethanolic solutions are then added to the aqueous solution above. Sufficient water is then added to bring to final volume with continuous agitation.

EXAMPLE C — Oral Solution Dosage Form Containing 500 mg. of Active Ingredient Per Five ml.

|  | Per 5 ml. |  |
|---|---|---|
| Copolymer of Ethylene and Maleic Anhydride (water soluble) | 750 | mg. |
| Propylene Glycol | 100 | mg. |

|                  | Per 5 ml. |
|------------------|-----------|
| Saccharin Sodium | 0.05 mg.  |
| Propylparaben    | 5 mg.     |
| Flavoring Agent  | 0.03 mg.  |
| FD & C Yellow No. 5 | 0.2 mg. |
| Purified Water   | qs        |

The water soluble copolymer (EMA-31) is dissolved in a portion of water by gentle agitation. The saccharin sodium is dissolved in a small portion of water. The FD & C Yellow No. 5 is dissolved in a small portion of water. These two solutions are added to the above solution. The propylparaben is dissolved in a small portion of propylene glycol, the flavoring agent is dissolved in the remaining propylene glycol. The two propylene glycol solutions are then added to the above aqueous solution. Sufficient water is then added to bring to final volume with continuous agitation.

EXAMPLE D — Dry-filled Capsules Containing 250 mg. of Active Ingredient Per Capsule

|                             | Per Capsule |
|-----------------------------|-------------|
| Polyacrylic Acid (Example 12) | 250 mg.   |
| Magnesium Stearate          | 2.5 mg.     |
|                             | 252.5 mg.   |

Weigh and pass the polyacrylic acid and magnesium stearate through a No. 40 mesh screen. Blend the ingredients in a twin-shell blender for ten minutes. Full each gelation capsule No. 0 to 252.5 mg. of blended product.

The polymers are known or may be prepared by methods well known to those skilled in the art. See, for example, U. S. Pat. Nos. 2,798,053; 3,224,941; 3,842,022 and 3,957,973 which patents are hereby incorporated by reference.

The following examples illustrate the products of this invention and the process for preparing same; however, it is to be understood that by substituting other monomers for those recited in the examples, all of the products of this invention can be prepared.

EXAMPLE 1 — Polyacrylic Acid - MW = 400,000

Into a five-liter, roundbottom flask, equipped with an agitator, a thermometer and means of adding monomer and catalyst solution, is added 2260 ml. of deionized water. Heat is applied to raise the temperature of the initial charge water to 95° C. An initial catalyst of 0.83 g. of ammonium persulfate is then added. One minute later a monomer charge of 905 grams of glacial acrylic acid and a catalyst solution of 1.20 grams of ammonium persulfate (APS) in 100 ml. of deionized water are added gradually over a period of about 100 minutes. The temperature is maintained at 92°-96° C. during the additions. After additions are completed, the product is held at 90°-96° C. for an additional 60 minutes. At the end of the 60 minute hold, it is cool. While cooling, 350 ml. of deionized water is added. The final product is a clear viscose solution with a polymer content of 24%.

By following substantially the procedure of Example 1 and by varying the amount of catalyst or by using different monomers or mixtures of monomers, other polyacrylic acids, homopolymers or copolymers of this invention can be prepared. A clean up catalyst is sometimes employed and is added after completion of the monomer and catalyst feeds. The following table indicates the amount of catalyst employed, the clean up catalyst, the solids and the viscosity.

TABLE I

| Ex. No. | Catalyst % By Wt. | Clean Up Catalyst | Solids | Viscosity |
|---------|-------------------|-------------------|--------|-----------|
| 2       | 0.225             | None              | 24.4   | 14,600    |
| 3       | 0.225             | None              | 24.2   | 10,200    |
| 4       | 0.24              | 0.1% APS          | 20.5   | 4,000     |
| 5       | 0.57              | 0.05% APS         | 29.9   | 7,000     |
| 6       | 0.60              | 0.1% APS          | 30.1   | 5,200     |
| 7       | 0.65              | 0.5% APS          | 29.4   | 4,100     |
| 8       | 0.90              | 0.1% NaHSO$_3$    | 29.3   | 2,080     |
| 9       | 1.10              | 0.04% to BHP/ 0.3% Formopan | 30.0 | 1,660 |
| 10      | 1.80              | 0.1% APS          | 30.8   | 540       |
| 11      | 2.00              | 0.1% APS          | 30.4   | 400       |
| 11a     | 0.75              | None              | 22.0   | 800       |

APS - Ammonium persulfate
BHP - t-Butyl hydroperoxide
Formopan - Sodium sulfoxylate formaldehyde

EXAMPLE 12 — Polyacrylic Acid

To a 12 liter, three necked flask equipped with a large Teflon stirring blade, gas inlet tube, 12 liter heating mantle, thermometer with Thermowatch sensor attached, and stirring motor is added 2515 g. of deionized water (DI) and 946 g. of table salt. The flask and solution are sparged and stirred well with nitrogen for one hour to displace oxygen while dissolving the salt. To the moderately stirred solution at room temperature is added slowly 18.5 g. of Primafloc C-7 slurried in 100 g. of DI water. When the salt is completely dissolved with Primaflox C-7 completely dispersed 7.0 g. (0.5 mole % of acrylic acid) of lauroyl peroxide dissolved in 214.5 g. of toluene, 491 g. (6.82 moles of acrylic acid) and 4.9 g. of 1,1,1-trimethylolpropanetrimethacrylate is mixed and the solution added below surface of the salt solution via a long stem funnel. The organic and water mixture is stirred for 10 minutes at 113 RPM, stopped, and intermittenly stirred for 30-60 seconds until a dispersion is seen. (Voluminous shiny, sparkling points visible by illumination with a flashlight indicated that the desired suspension is present.) The reaction mixture is heated gradually to 55° C. Heating is continued while adding 26.5% brine solution from a dropping funnel (1800 ml. of brine solution is added). The temperature is then raised 5°-10° in steps for 15 to 30 minute periods each, until 90° C. is reached. (Care is necessary during the heat input to prevent product over-swelling and foaming.) The fluffy mixture is heated for two hours at 90° C. to decompose any remaining lauroyl peroxide. The flask is then fitted with a take-off condenser and 950 g. of water/toluene azeotrope distilled with the pot temperature at 112° C. About 600 ml. of brine is added during the distillation, in 100-200 ml. increments, to maintain control and retain the organic product/salt ratio. The reaction mixture is cooled to room temperature. The salt solution is vacuum siphoned easily through a fine mesh screen or muslin to yield 3100 ml. of filtrate. The system is then changed to a 12 liter resin kettle equipped with a heavy duty metal stirrer necessary to stir the fluffy heavy product. 5000 ml. of DI water is added and the reaction stirred for at least one-half hour. Filtration yields 4600 ml. of filtrate (pH 2.8). Four more washes and filtrations are made as above and listed in Table A. (Swelling increased with each wash as salt levels are successively reduced.)

TABLE A

| Wash | Filtrate | pH |
|---|---|---|
| 1 | 4600 ml. | 2.8 |
| 2 | 4000 ml. | 3.2 |
| 3 | 5000 ml. | 3.3 |
| 4 | 4500 ml. | 3.5 |
| 5 | 4500 ml. | 3.8 |

The water-laden product is then allowed to air dry overnight, spread thinly on aluminum foil. The product is then vacuum dried at 80°–90° C. for 24 hours to yield 450 g. (90.7% yield) of polyacrylic acid as a white brittle solid. % NaCl found: 3.1; water found by KF: 3.1%; Free AA: 0.1% (glc).

EXAMPLE 13 — Polymethacrylic Acid (S.I. = 59)

One ml. of a solution containing 0.0452 g. of ethanolaminetriacrylate dissolved in glacial methacrylic acid (MAA) combined with sufficient additional MAA to bring the total weight to 39.86 g. This is diluted with 78.0 g. of distilled water, charged to a polyethylene reaction and degassed with nitrogen for 1.5 hours. After degassing, an initiator of cumen hydroperoxide (0.1118 g.) and isoascorbic acid (0.0102 g.) is added at one minute intervals with gentle swirling to mix. The nitrogen atmosphere is replenished and the reaction mixture placed in a warm (35°–40° C.) water bath and the contents periodically mixed by gentle shaking. The solution grows more viscous, finally reaching a gel consistency in five hours. After standing in a 35° C. water bath overnight to insure complete polymerization, the gel is removed, cut into pieces and dried in a 60° vacuum oven for 72 hours before brinding and passing through a 60 mesh screen to yield 41.5 g. of polymethacrylic acid. Swelling index in deionized water is 59. Maximum solubles (24 hours of extraction) is 13.6%.

PHARMACOLOGICAL DATA

The effect of the products of this invention is shown in the following table. The test materials are present in concentrations of 1% of a normal protein test diet. The test animal is a female Sprague-Dawley rat. Eight rats are used per compound tested. All feces excreted on the fourth and fifth days of treatment are collected and analyzed for calcium (atomic absorption) and phosphate (Fiske-Subbarow method).

| Influence of Carboxylic Resins and Cellulose Phosphate on Fecal Electrolyte Excretion in the Laboratory Rat | | | |
|---|---|---|---|
| | Fecal Electroyles (mg./day) | | |
| Products Tested | Calcium (Ca) | Phosphorous (P) | Ca/P |
| Control - (Microcrystalline Cellulose Avicel) | 46.7 ± 4 | 21.5 ± 5 | 2.19 ± .1 |
| Products of this Invention | | | |
| Example 1 | 58 ± 5 | 15.2 ± 3 | 4.26 ± .3 |
| Example 12 (Acid form) | 53 ± 6 | 15.6 ± 5 | 3.47 ± .1 |
| Example 12 (Na form) | 57.1 ± 7 | 13.6 ± 6 | 3.45 ± .2 |
| Example 13 | 52.4 ± | 17.9 ± 2 | 2.91 ± .1 |
| Ethylene-maleic anhydride (EMA-31) | 51.6 ± 4 | 13.2 ± 2 | 3.80 ± 0.2 |
| Ethylene-maleic anhydride (EMA-81) | 51.1 ± 3 | 10.7 ± 2 | 4.23 ± 0.2 |
| Known Ca Sequestrant Sodium Cellulose Phosphate | 52.8 ± 1 | 23.2 ± 3 | 2.72 ± .3 |

The results show that when compared to microcrystalline cellulose (the control), all of the carboxylic acid containing polymers of this invention and also sodium cellulose phosphate cause an increase in fecal calcium excretion. All of the carboxylic acid containing polymers also caused a decrease in fecal phosphate excretion when compared to either control or sodium cellulose phosphate. This inverse relationship between fecal calcium and fecal phosphate is expressed as the calcium/phosphate ratio. The ability of a material to increase fecal calcium excretion and decrease fecal phosphate excretion is highly desirable for the treatment of kidney stones. In essence, the active material reduces the calcium load on the kidney and increases the amount of phosphate going through the kidney. The net effect will be to dissolve calcium-containing stones and/or prevent formation of calcium deposits in the kidney or the urinary tract.

Some theories suggest that an increase in urinary phosphate excretion is even more important than the decrease in urinary calcium insofar as dissolution of kidney stones is concerned. We have found that the decrease in fecal phosphate caused by the administration of colloidally water soluble and soluble carboxylic acid-containing polymers results in a marked increase in urinary phosphate.

Following is an experiment comparing the urinary $PO_4$ excretion and amount of $PO_4$ present in the feces of rats fed with cellulose or a swellable polymer of this invention (ethylene-maleic anhydride - EMA-81).

The rats (6 in each test) were trained to eat during a four hour period each 24 hours. During the remaining 20 hours per day, the rats were placed in metabolism cages so that clean urine could be collected. After eight days, the rats were killed and the amount of $PO_4$ present in their ceacum and large intestine (fecal $PO_4$) was determined. The results in Table II show that EMA-81 caused a 3-fold increase in the urinary $PO_4$ concentration with a concomitant decrease in fecal $PO_4$.

TABLE II

| Dose - 25% of Normal Diet | Urinary $PO_4$ $\mu$moles/ml. | Fecal $PO_4$ $\mu$moles/g. |
|---|---|---|
| Control | 44.5 ± 15[1] | 271 ± 29 |
| EMA-81 | 140 ± 42 | 51 ± 3 |

[1] Data presented are mean ± SEM.

What is claimed is:

1. A method for decreasing urinary calcium content and increasing urinary phosphate content which comprises orally administering to a person whose urine contains insoluble calcium containing precipitates or has a propensity for forming calcium containing precipitates, an effective amount of an agent selected from the water soluble and lightly crosslinked colloidally water soluble homopolymers and copolymers of olefinically unsaturated carboxylic acids and their nontoxic pharmaceutically acceptable salts wherein said homopolymers and copolymers, if soluble have a degree of polymerization of from about 10 to about 100,000 and, if colloidally water soluble, have a swelling index of from about 10 to about 1500.

2. The method of claim 1 wherein the polymer is prepared from a monoolefinic acrylic acid having the general structure:

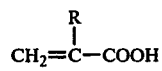

wherein R is a substituent selected from the class consisting of hydrogen, halogen, hydroxy and alkyl.

3. The method of claim 2 wherein all the polymers are water soluble.

4. The method of claim 3 wherein the polymer is prepared from methacrylic acid.

5. The method of claim 3 wherein the polymer is prepared from ethylene maleic anhydride.

6. The method of claim 2 wherein the polymer is a lightly crosslinked colloidally water soluble polymer having a swelling index of from about 10 to about 500.

7. The method of claim 6 wherein the polymer is prepared from acrylic acid and a crosslinker selected from 1,1,1-trimethylolpropane trimethacrylate, polyallyl sugars, and triethanolamine triacrylate.

8. A composition for decreasing urinary calcium content and increasing urinary phosphate content which comprises a unit dosage of from about 10 mg. to about 400 mg./kg. of body weight of an agent selected from the water soluble and lightly crosslinked colloidally water soluble homopolymers and copolymers of olefinically unsaturated carboxylic acids containing at least one carbon-to-carbon olefin double bond and at least one carboxy group, wherein the polymers have a degree of polymerization in the range of from about 10 to about 100,000 and a swelling index of from about 10 to about 500 and the nontoxic, pharmaceutically acceptable salts thereof.

* * * * *